US008998864B2

(12) United States Patent
Perkins et al.

(10) Patent No.: US 8,998,864 B2
(45) Date of Patent: Apr. 7, 2015

(54) OPHTHALMIC SURGICAL CASSETTES FOR OPHTHALMIC SURGERY

(75) Inventors: James T. Perkins, St. Charles, MO (US); Toh Seng Goh, Ballwin, MO (US); David Hertweck, Valley Park, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 1361 days.

(21) Appl. No.: 12/270,998

(22) Filed: Nov. 14, 2008

(65) Prior Publication Data
US 2010/0125257 A1 May 20, 2010

(51) Int. Cl.
*A61M 1/00* (2006.01)
*A61F 9/007* (2006.01)

(52) U.S. Cl.
CPC ........... *A61M 1/0031* (2013.01); *A61M 1/0045* (2014.02); *A61M 1/0062* (2013.01); *A61F 9/007* (2013.01); *A61M 1/0076* (2013.01); *A61M 2205/12* (2013.01); *A61M 2210/0612* (2013.01)

(58) Field of Classification Search
None
See application file for complete search history.

(56) References Cited

U.S. PATENT DOCUMENTS

| 4,627,833 | A | * | 12/1986 | Cook | 604/34 |
|---|---|---|---|---|---|
| 4,702,733 | A | | 10/1987 | Wright | |
| 4,758,220 | A | * | 7/1988 | Sundblom et al. | 604/65 |
| 4,773,897 | A | | 9/1988 | Scheller et al. | 604/34 |
| 4,857,047 | A | * | 8/1989 | Amoils | 604/30 |
| 5,163,900 | A | * | 11/1992 | Wortrich | 604/30 |
| 5,417,246 | A | * | 5/1995 | Perkins et al. | 137/870 |
| 5,582,601 | A | | 12/1996 | Wortrich et al. | 604/318 |
| 5,718,238 | A | * | 2/1998 | Perkins et al. | 600/573 |
| 5,897,524 | A | * | 4/1999 | Wortrich et al. | 604/30 |
| 2003/0105437 | A1 | * | 6/2003 | Neubert | 604/319 |
| 2005/0065462 | A1 | * | 3/2005 | Nazarifar et al. | 604/30 |
| 2005/0118048 | A1 | * | 6/2005 | Traxinger | 417/477.2 |
| 2006/0100570 | A1 | | 5/2006 | Urich | |
| 2007/0287959 | A1 | * | 12/2007 | Walter et al. | 604/131 |
| 2008/0147023 | A1 | * | 6/2008 | Hopkins et al. | 604/318 |
| 2008/0312594 | A1 | * | 12/2008 | Urich et al. | 604/149 |
| 2010/0030134 | A1 | | 2/2010 | Fitzgerald | |
| 2010/0152685 | A1 | * | 6/2010 | Goh | 604/319 |

FOREIGN PATENT DOCUMENTS

WO WO/2007/143677 A2 12/2007

OTHER PUBLICATIONS

International Search Report (PCTISA/210) and Written Opinion (PCT/ISA/237) mailed on May 6, 2010.

* cited by examiner

*Primary Examiner* — Melanie Hand
*Assistant Examiner* — Paula L Craig
(74) *Attorney, Agent, or Firm* — Michael L. Smith

(57) ABSTRACT

An ophthalmic surgical cassette for collecting aspirant fluid and/or tissue during an ophthalmic surgical procedure. The ophthalmic surgical cassette includes a rigid walled container having an interior volume for collecting aspirant fluid and/or tissue and an aspiration manifold coupled to the rigid walled container. The aspiration manifold is connected to an aspiration tube in fluidic communication with the interior volume, a first aspiration line for coupling a first surgical handpiece, a second aspiration line for coupling a second surgical handpiece, and a reflux bulb in fluidic communication with the first and second aspiration lines.

8 Claims, 4 Drawing Sheets

OPHTHALMIC SURGICAL CASSETTES FOR OPHTHALMIC SURGERY

BACKGROUND

1. Field

The present invention is directed to ophthalmic surgical cassettes for use with pump systems. More specifically, the present disclosure is directed towards an ophthalmic surgical cassette having a reflux bulb.

2. Description of the Related Art

The statements in this section merely provide background information related to the present disclosure and may not constitute prior art.

Ophthalmic surgical cassettes for use with pump systems during ophthalmic surgical procedures are generally known. Each ophthalmic surgical cassette common includes a container for retaining aspirant fluid and tissue retrieved from a surgical site during an ophthalmic surgical procedure. It is common for ophthalmic surgical cassettes to also include an aspiration tube, which is attached to a surgical handpiece during the ophthalmic surgical procedure.

It is common for the aspiration line to have ability to reflux aspirant tissue and fluid back toward the surgical site upon request from a surgeon. To achieve reflux, each aspiration tube typically includes a reflux bulb and a block pinch point. A pump system, in which the ophthalmic surgical cassette is positioned, generally includes plungers to depress the reflux bulb against the block pinch point. When reflux is requested, a first plunger depresses aspiration tubing at a flow pinch point to isolate the aspiration path tubing from the container. Then, a second plunger depresses the reflux bulb causing a reverse flow of aspirant fluid and tissue in the aspiration tube generally equal to a displacement of the compression. For multiple aspiration tubes, each of the aspiration tubes includes a reflux bulb and a block pinch point, thereby requiring at least two plungers in the pump system for each aspiration tube.

If the cassette does not include the first plunger to isolate the aspiration path from the container, when reflux is requested by the surgeon, suction may be generated, reducing effectiveness of the reflux in the aspiration tube. In addition, reflux is requested repeatedly in a short period of time, air may be pulled into the aspiration tube from the container, further reducing effectiveness of the repeated reflux requests because of the compressibility of air.

Therefore, there exists the need for an improved ophthalmic surgical cassette with minimal components and effective reflux performance.

BRIEF DESCRIPTION OF THE DRAWINGS

The drawings described herein are for illustration purposes only and are not intended to limit the scope of the present disclosure in any way.

DETAILED DESCRIPTION OF THE PREFERRED EMBODIMENT

The following description is merely exemplary in nature and is not intended to limit the present disclosure, application, or uses.

Figure 1:
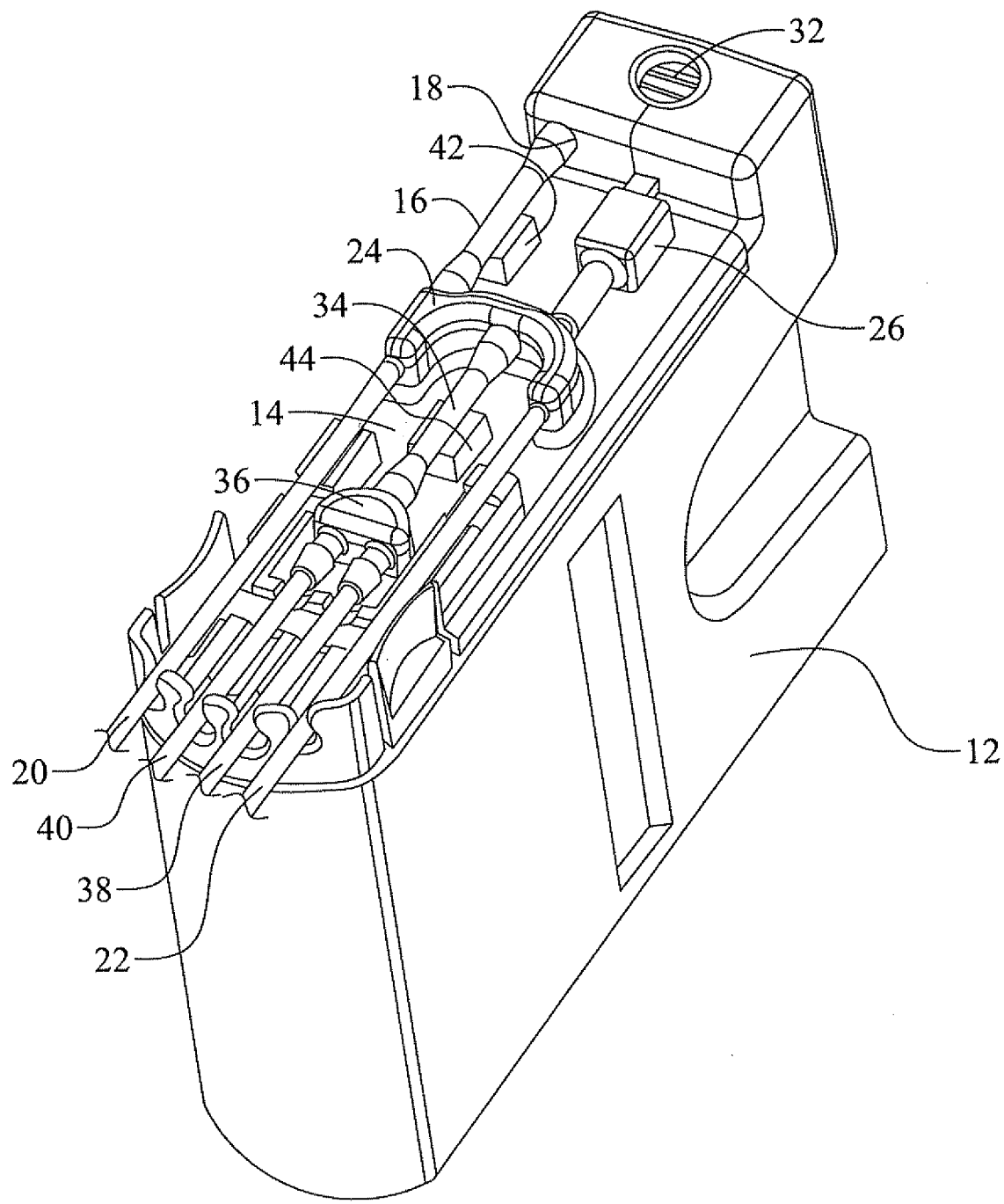
FIG. 1 is a perspective view of an ophthalmic surgical cassette according to the present disclosure.

According to one embodiment of the present disclosure, an ophthalmic surgical cassette 10 is illustrated in FIG. 1. The ophthalmic surgical cassette 10 includes a rigid walled container 12 having an interior volume for collecting aspirant fluid and/or tissue and a main manifold 14 coupled to the rigid walled container 12. The manifold 14 includes an aspiration tube 16 in fluidic communication with the interior volume via an inlet 18 of the rigid walled container 12. The manifold includes two aspiration lines 20, 22. The aspiration line 20 is connected to the aspiration line 22 through an aspiration manifold 24. The aspiration manifold 24 is also connected to the aspiration tube 16, such that aspirant fluid and/or tissue may flow in a first direction from a surgical site to the interior volume of the container 12 via the aspiration tube 16 during an ophthalmic surgical procedure. Structure 32 typically is an orifice over which gas is blown in order to create a venturi aspiration within the container 12.

The manifold 14 also includes a reflux bulb 26 in fluidic communication with the two aspiration lines 20, 22. In this embodiment, the reflux bulb 26 is connected to aspiration lines 20, 22 through the aspiration manifold 24. Reflux can also be attained by introducing irrigation fluid into aspiration manifold 24, as is known. The reflux bulb 26 is included to generate fluid displacement, i.e., reflux, in a direction opposite the first direction in at least one of the aspiration lines 20, 22, as explained below. Reflux may be useful to a surgeon during an ophthalmic surgical procedure to clear an occlusion along the aspiration path from an eye to a surgery system including the ophthalmic surgical cassette 10, e.g., a piece of tissue causing an occlusion captured by aspiration through a surgical handpiece having a needle.

Figure 2:
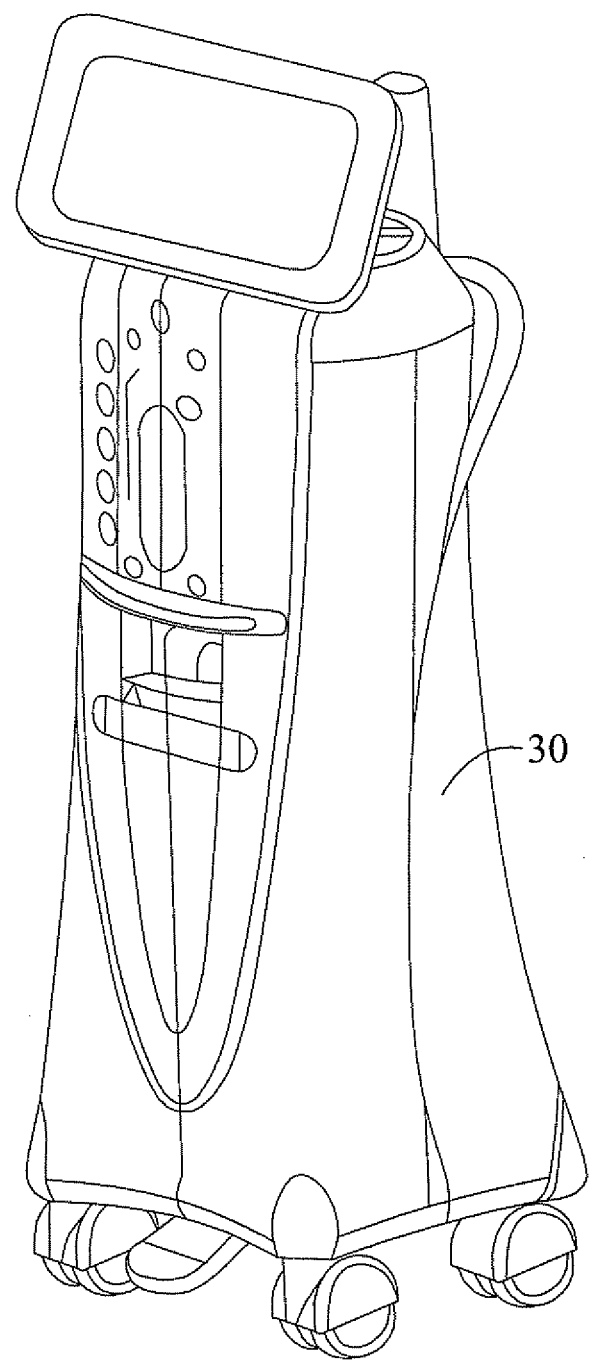
FIG. 2 is a perspective view of an ophthalmic surgery console according to the present disclosure.

In use, the ophthalmic surgical cassette 10 is included in an ophthalmic surgical console. The ophthalmic surgical cassette 10 is configured to interface with a pump (not shown) included in an ophthalmic surgical console 30, which is shown in FIG. 2. In this particular embodiment, the pump is a venturi pump. In other embodiments, a different type of pump may be employed, such as a vacuum pump or other suitable pump. In use, the aspiration line 20 is coupled to a first surgical handpiece, and the aspiration line 22 couples to a second surgical handpiece. Surgical handpieces may include phacoemulsification handpieces, vitrectomy devices, or other types of ophthalmic handpieces which are intended to employ aspiration.

Figure 3:
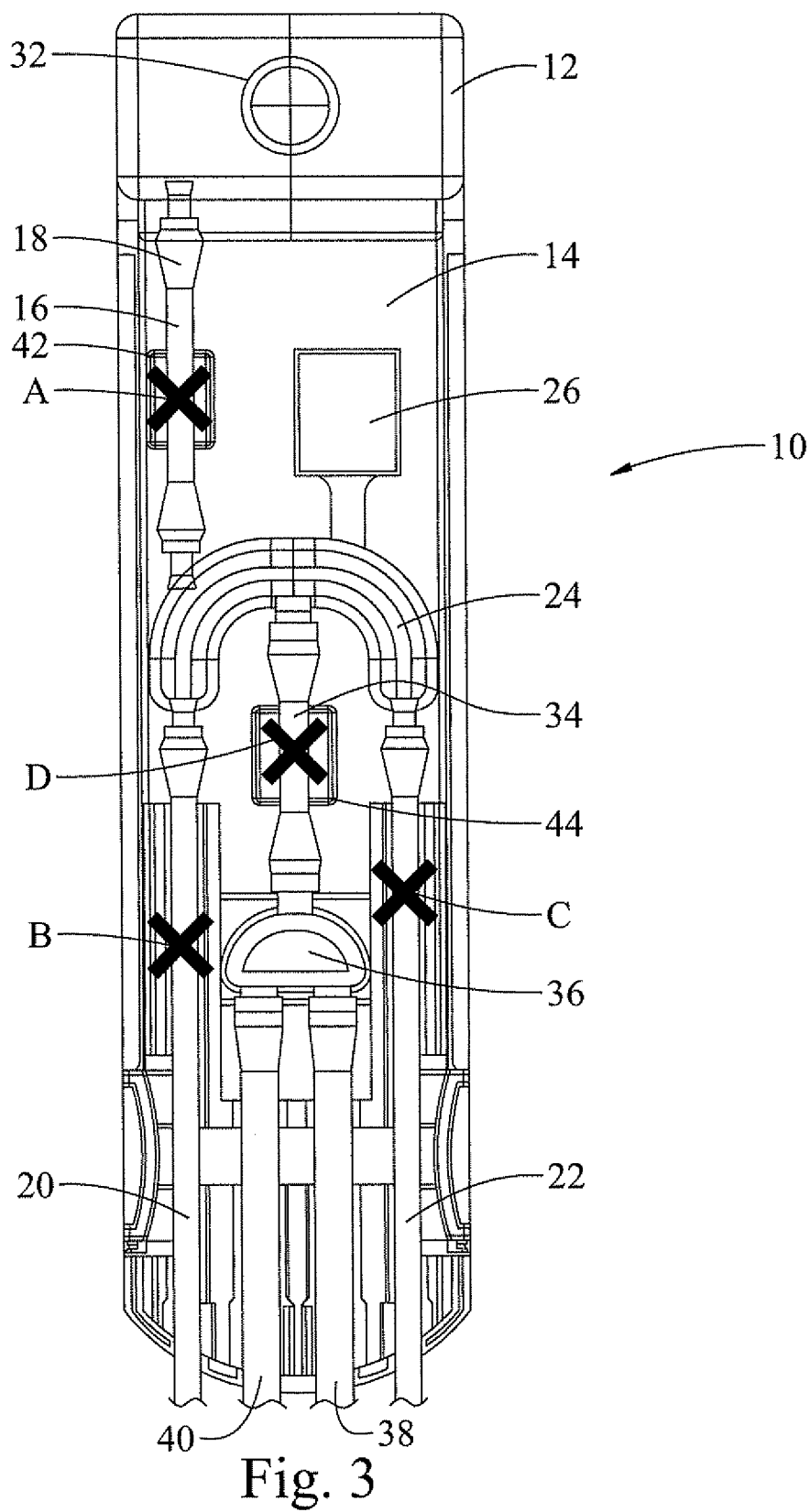
FIG. 3 is a top elevation view of a manifold according to the present disclosure.

FIG. 3 shows a top view of the manifold 14, in accordance with the present disclosure, including a number of dark "X"s to illustrate potential pinch points to control the flow of fluid in the aspiration path. The manifold 14 is configured so that when the aspiration tube 16 at A and the aspiration line 20 at "B" are pinched via plungers (not shown) included in the ophthalmic surgical console 30, depressing the reflux bulb 26 causes a flow of fluid in a direction forward a surgical site (not shown) in the aspiration line 22. Conversely, when the aspiration tube 16 at "A" and the aspiration line 22 at "C" are pinched, depressing the reflux bulb 26 causes reflux in aspiration line 20. In this manner, the ophthalmic surgical cassette 10 within console 30 may provide reflux for two aspiration lines 20, 22 with only one reflux bulb 26. It is also possible to provide simultaneous reflux flow in lines 20 and 22 by only pinching the aspiration path at A.

It should be appreciated that only one reflux bulb may be included in other embodiments, according to the present disclosure, to provide reflux in more than two aspiration lines. More than two aspiration lines may be included depending on the ophthalmic surgical console and/or the type of ophthalmic surgical procedure to be performed. Also, only one plunger is required in a console for each additional aspiration line to isolate the additional aspiration line when a different aspiration line is being refluxed, as described above.

The manifold 14 preferably includes an irrigation tube 34 connected to the aspiration lines 20, 22 via the aspiration manifold 24. As shown in FIG. 3, the reflux bulb 26 is offset from the irrigation tube 34. In use, the irrigation tube 34 couples to an irrigation source, e.g., a bottle of balanced salt solution (BSS). Accordingly, when the reflux bulb 26 is depressed, fluid flow from the irrigation tube 34 may aid in the fluid displacement in the direction towards a surgical site in aspiration lines 20, 22. The in-flow of irrigation fluid may also speed at least partial re-inflation of the reflux bulb 26. In this manner, the reflux bulb 26 is generally primed with fluid, regardless of when the last reflux occurred. Thus, when the reflux bulb 26 is depressed multiple times in a short period, the irrigation tube 34 ensures consistent reflux, while inhibiting the introduction of air into one or both of the aspiration lines 20, 22. The irrigation tube 34 may also be isolated from reflux via a pinch point at "D." Generally, the irrigation path is isolated from the aspiration lines 20, 22, unless reflux or venting is requested. In some implementation however, the irrigation tube 34 may be isolated when the reflux bulb 26 is depressed only once within a predetermined period of time.

A manifold of the present disclosure may also be employed to provide different reflux pressures for one or more different techniques used during an ophthalmic surgical procedure. As stated above, reflux may be used to clear an occlusion. Additionally or alternatively, a low pressure reflux may be used to clear blood along the retina, a more delicate technique. The reflux pressure generated by a reflux bulb may be increased or decreased in several ways.

Figure 4:
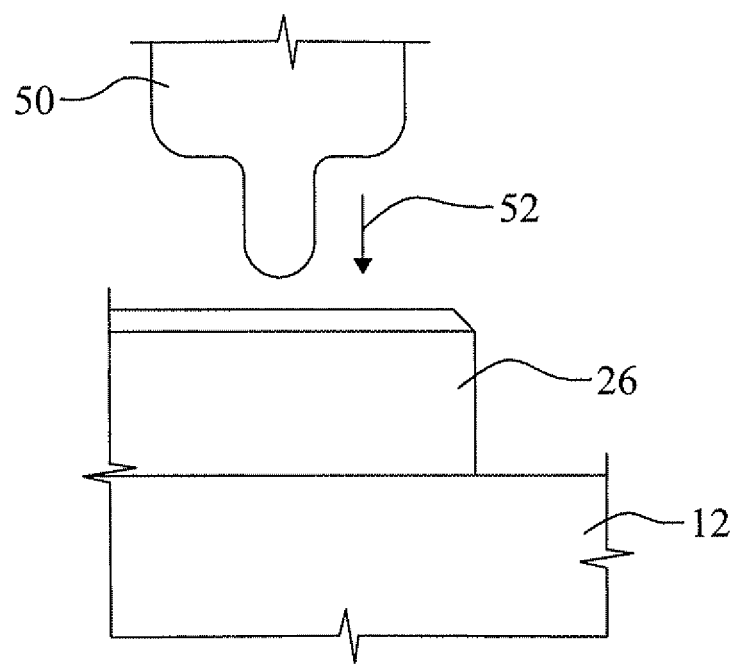
FIG. 4 is a partial view of a reflux bulb according to the present invention in use.

A first example, allowing a user to increase or decrease the reflux pressure generated, in at least one of the aspiration lines 20 and 22, is having a mechanical plunger 50, shown in FIG. 4, controlled in a proportional manner by movement of a foot pedal (not shown). The further a user moves a foot pedal in a linear direction, the faster plunger 50 would move in the direction of arrow 52 to depress reflux bulb 26. Reflux pressure is proportional to the speed at which plunger 50 depresses bulb 26. Plunger 50, in this and the following examples, would be contained within console 30 at position to allow the plunger to interact with bulb 26, as shown in FIG. 4.

A second example of varying the reflux pressure is by enabling console 30 to vary the distance of travel of plunger 50. In this second example, a user may be able to choose between a number of settings for reflux pressure, such as Full, Medium, and Light on an input screen (not shown). If the user chooses Full, then plunger 50 would be made to travel a greatest distance in the direction of arrow 52 and depress bulb 26 to a greatest extent, compared to the Medium and Light settings. Depressing bulb 26 to a greatest extent results in greater reflux pressure compared to the other settings.

A third example for achieving variable reflux pressure is achieved by controlling aspiration pinch valves (not shown) at pinch points B and C. If the valves and B and C are set so that both lines 20 and 22 are open a minimum reflux pressure will be achieved; while if one line 20 or 22 is pinched closed then a maximum reflux pressure will be achieved in the line that is open.

A fourth example for achieving different levels of reflux pressure is by constructing reflux bulb 26 of different materials, sizes, and shapes. So, for example, bulb 26 will be depressed more if made of a compliant material compared to being depressed less, if made of a comparatively more rigid material. Of course, this example assumes the same amount of force is applied to the bulbs of different material by plunger 50. This example of using different materials, sizes, or shapes for reflux bulb 26 may be useful in designing reflux bulbs for particular surgeries to be performed.

The irrigation tube 34 is connected via an irrigation manifold 36 to irrigation inlet tube 38 and an irrigation outlet tube 40. The irrigation inlet tube 38 is coupled to BSS or other irrigation source during an ophthalmic surgical procedure. The irrigation outlet tube 40 transmits irrigation fluid during the ophthalmic surgical procedure to an ophthalmic surgical instrument, e.g., a cannula. Thereby, the ophthalmic surgical cassette 10 may provide irrigation fluid to a surgical site and to the aspiration path during an ophthalmic surgical procedure, rather than requiring a separate irrigation source for each. It should however, be appreciated that an ophthalmic surgical cassette may couple to a dedicated irrigation source for irrigation each of a surgical site and the aspiration path.

The manifold 14 is preferably removably coupled to the rigid walled container 12. During an ophthalmic surgical procedure, a container may become filled with aspirant fluid and tissue, such that it is desirable to empty the container before continuing in the ophthalmic surgical procedure. When the manifold 14 is removable, as in FIG. 1, the rigid walled container 12 may be conveniently removed from the pump 28, without the added operation of disconnecting one or more surgical handpieces and/or other ophthalmic surgical instrument from the aspiration line 20, 22 and/or irrigation inlet/outlet tubes 38, 40 included in the manifold 14.

The reflux bulb 26 is preferably formed from silicone. A different type of material may be included depending on the application and requirements of the user. Other materials suitable to be included in a flow control device may be PVC, polyurethane and/or other suitable surgical materials.

In this embodiment of the present disclosure, the manifold 14 includes block 42, positioned adjacent to the aspiration tube 16. When a plunger (not shown) depresses the aspiration tube 16, block 42 provides a contact surface to resist movement of the plunger, thereby causing compression of the aspiration tube 16 and forming pinch point A. Similarly, the manifold 14 includes block 44, positioned adjacent to the irrigation tube 34 to form pinch point D. Similar blocks are provided for pinch points B and C, though not shown.

Although several aspects of the present disclosure have been described above with reference to ophthalmic surgical cassettes, it should be understood that various aspects of the present disclosure are not limited to ophthalmic surgical cassettes, and can be applied to a variety of other ophthalmic surgical systems, devices, and methods.

By implementing any or all of the teachings described above, a number of benefits and advantages can be attained, including improved reliability, reduced down time, elimination or reduction of redundant components or systems, avoiding unnecessary or premature replacement of components or systems, and a reduction in overall system and operating costs.

We claim:

1. An ophthalmic surgical cassette for collecting aspirant fluid and/or tissue during an ophthalmic surgical procedure, the ophthalmic surgical cassette comprising:
 a rigid walled container having an interior volume for collecting aspirant fluid and/or tissue; and
 an aspiration manifold coupled to the rigid walled container, the aspiration manifold connected to an aspiration tube in fluidic communication with the interior volume, a first aspiration line for coupling a first surgical handpiece, a second aspiration line for coupling a second surgical handpiece, an irrigation tube for coupling to an irrigation source, and only a single reflux bulb connected to the aspiration manifold for providing reflux to both the first and second aspiration lines when the bulb is depressed.

2. The invention of claim 1, wherein the cassette is configured such that when the aspiration tube and one of the first and second aspiration lines are pinched, depressing the reflux bulb causes reflux in the other of the first and second aspiration lines.

3. The invention of claim 1, wherein the aspiration manifold is formed on a main manifold that is releasably coupled to the rigid walled container.

4. The invention of claim 1, wherein the aspiration manifold is further connected to an irrigation tube for coupling an irrigation source and for at least partially priming the reflux bulb.

5. The invention of claim 4, the irrigation tube including a pinch point to allow control of fluidic communication between the irrigation tube and the aspiration manifold.

6. An ophthalmic surgical cassette for collecting aspirant fluid and/or tissue during an ophthalmic surgical procedure, the cassette comprising:

a rigid walled container having an interior volume for collecting aspirant fluid and/or tissue; and an aspiration manifold releasably coupled to the rigid walled container, the aspiration manifold connected to a reflux bulb, an irrigation tube, and at least two aspiration lines, wherein the reflux bulb is capable of inducing reflux in either or both of the at least two aspiration lines.

7. The invention of claim 6 in use in an ophthalmic surgical console, wherein the console includes a plunger for interacting with the reflux bulb, such that a speed of movement of the plunger can be varied to cause a variation in a reflux pressure generated in at least one of the aspiration lines.

8. The invention of claim 6 in use in an ophthalmic surgical console, wherein the console includes a plunger for interacting with the reflux bulb, such that varying a distance of travel of the plunger causes a variation in a reflux pressure generated in at least one of the aspiration lines.

* * * * *